United States Patent [19]

Heyne et al.

[11] Patent Number: 4,557,725

[45] Date of Patent: Dec. 10, 1985

[54] I. V. PUMP CASSETTE

[75] Inventors: John A. Heyne; Leland D. Chamness, both of Mountain View, Calif.

[73] Assignee: Oximetrix, Inc., Mountain View, Calif.

[21] Appl. No.: 606,923

[22] Filed: May 4, 1984

[51] Int. Cl.⁴ .............................................. A61N 5/00
[52] U.S. Cl. ...................................... 604/67; 604/151; 604/246; 128/DIG. 12
[58] Field of Search ................... 604/65, 67, 131, 245, 604/246, 151–153; 128/DIG. 12

[56] References Cited

U.S. PATENT DOCUMENTS

| | | | |
|---|---|---|---|
| 4,038,982 | 8/1977 | Burke et al. | 604/65 |
| 4,321,461 | 3/1982 | Walter, Jr. et al. | 604/65 |
| 4,336,800 | 6/1982 | Pastrone | 604/141 |
| 4,453,932 | 6/1984 | Pastrone | 128/DIG. 12 |
| 4,457,753 | 7/1984 | Pastrone | 128/DIG. 12 |
| 4,460,358 | 7/1984 | Somerville et al. | 604/245 |
| 4,474,309 | 10/1984 | Solomon | 604/67 |
| 4,496,351 | 1/1985 | Hillel et al. | 604/65 |

Primary Examiner—C. Fred Rosenbaum
Assistant Examiner—Michelle N. Lester
Attorney, Agent, or Firm—Kelly Robert S.

[57] ABSTRACT

An I.V. pump cassette includes an enclosed pumping chamber with an inlet and outlet adapted to be connected to I.V. tubing. A reciprocable plunger extends from the top of the pumping chamber. The cassette is arranged to be received in a semi-cylindrical chamber in a driver mechanism wherein a horizontally extending support portion of the cassette can be supported in a semi-circular recess and clamped thereon by overlying clamp members of the driver mechanism. An upstanding semi-circular fence is provided at the front end of the cassette to activate a laterally pivotable switch in the appropriate driver mechanism and to create an interference with the wall of the semi-cylindrical chamber in an inappropriate driver mechanism.

12 Claims, 4 Drawing Figures

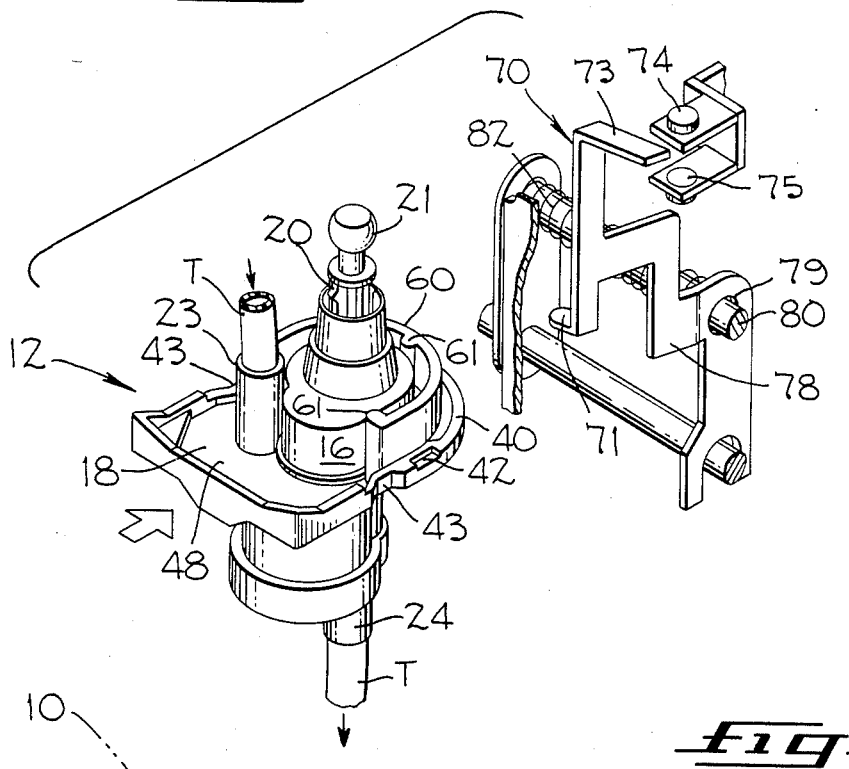
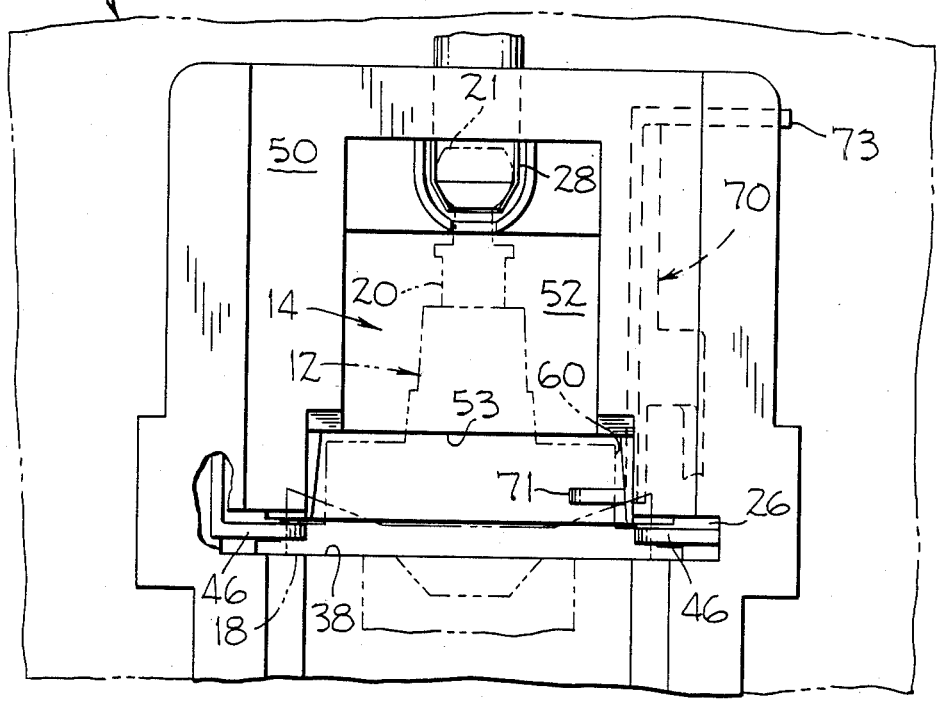

I. V. PUMP CASSETTE

BACKGROUND OF THE INVENTION

1. Field of the Invention

The present invention pertains to I.V. pumps for administering parenteral liquids in a controlled manner to a patient, and more particularly, it pertains to disposable I.V. pump cassettes which contain a small pumping chamber and a reciprocable piston or plunger for pumping liquid from the chamber and which are adapted to be inserted into pump driver mechanisms wherein the reciprocation of the piston or plunger can be controlled and monitored so as to achieve the desired delivery rate to the patient.

2. Description of the Prior Art

The intravenous delivery of fluids, such as nutrient solutions, has been a conventional and wide-spread practice in hospitals throughout the world for many years. Until relatively recently, such devices were typically of the gravimetric flow type wherein a bottle or bag containing the I.V. liquid was hung upon a pole or the like at an elevated location with tubing extending therefrom to a needle to be inserted into the vein of the patient. More recently, I.V. pumps have gained widespread acceptance since they are able to deliver fluids under very accurate and tightly controlled conditions so that potent medications or the like can be delivered intravenously to a patient wherein deviations from the desired delivery rate could have serious consequences.

In the conventional I.V. pumping apparatus now in use, there will typically be provided an I.V. pump driver mechanism including a variety of operating controls. The pump driver mechanism will be adapted to accept a disposable cassette containing the basic pumping chamber. The cassette, which is typically designed for one use only, is relatively small and must be economically manufactured to reduce its cost since it is designed to be disposable. The cassette will typically be activated by a reciprocatory driving device of the pump driver mechanism and will have tubing connections leading to the supply container and an intravenous set or the like for delivery of the I.V. fluids to the patient.

One typical prior art I.V. pump cassette is shown in U.S. Pat. No. 4,336,800 to Pastrone. As shown in this patent, the rigid plastic cassette comprises a positive displacement pumping chamber the volume of which is controlled by a diaphragm which is attached to a plunger extending upwardly from the body of the cassette. An inlet, for connection to appropriate tubing, is provided at the upper end of the cassette, and similarly, an outlet for connection to outlet tubing is provided at the lower end of the cassette. Extending laterally in a general horizontal plane is a supporting portion which is used to support the cassette in a pump driver mechanism and permit it to be clamped therein in an operable position by clamp members of the driver mechanism which are received in recesses on opposed sides of the support portion.

SUMMARY OF THE INVENTION

It has been discovered that, in certain I.V. pump applications, as for example when fluids are to be delivered to neonates and pediatrics wherein small, very critically controlled amounts must be delivered, it is essential to such delivery to insure that the most accurate pumping mechanism possible is provided. Nevertheless, the economic constraints imposed upon the construction of the pump cassettes, due to their one-use disposability, limit the machining and manufacturing quality that can be put into the cassette to assure highly accurate operation. Thus, it has been discovered that through testing, the cassettes having extremely high accuracy at very low flow rates can be separated from the remainder of any given batch and utilized solely in high accuracy, low flow critical care environments. Thus, two classes of pump drivers adapted to utilize essentially the same cassettes have been developed, one of such drivers being designed for delivering very small volumes and hence requiring the cassette which exhibits a high degree of accuracy at such low flow rates.

In accordance with the present invention, it is desirable to distinguish between these two types of otherwise identical cassettes by utilizing a system which will insure that only the best low flow adaptable cassettes are used with the low volume, high accuracy pump driver mechanism while the remainder of the cassettes are used solely with the conventional general purpose pump driving mechanism for use at normal I.V. flow rates. Thus, a switch activator device has been provided which is positioned on the forward portion of the supporting portion of the I.V. cassette so that it enters the pump driver mechanism first as the cassette is inserted therein. This switch activator mechanism comprises an upright fence or barrier presenting a smooth, semi-circular curved surface which may activate a pivotable switch in the pump driver mechanism to trigger a sensing mechanism so as to activate the pump driver mechanism only when the special, low flow pump cassette device has been inserted. On the other hand, the unique configuration of the switch activator acts, when the cassette is inserted into the wrong pump driver mechanism, to resist insertion by blocking the path of the cassette and resisting inward deflection of its arcuate shape to prevent the use of the low flow adaptable cassette in such mechanism. The switch activator is positioned at the forward end of the cassette relative to the clamp member receiving recesses so that the activator will function either to activate or reject the pump driver mechanism as the cassette is moved into its operable position.

BRIEF DESCRIPTION OF THE DRAWINGS

FIG. 3 is a front elevation of the cassette receiving chamber shown in FIG. 2 with the cassette being shown in phantom lines as received in said chamber.

FIG. 4 is an isometric view of the I.V. pump cassette of the present invention illustrating its operative relationship to the switch actuating mechanisms of the pump driver device.

DESCRIPTION OF THE PREFERRED EMBODIMENT

Figure 1:
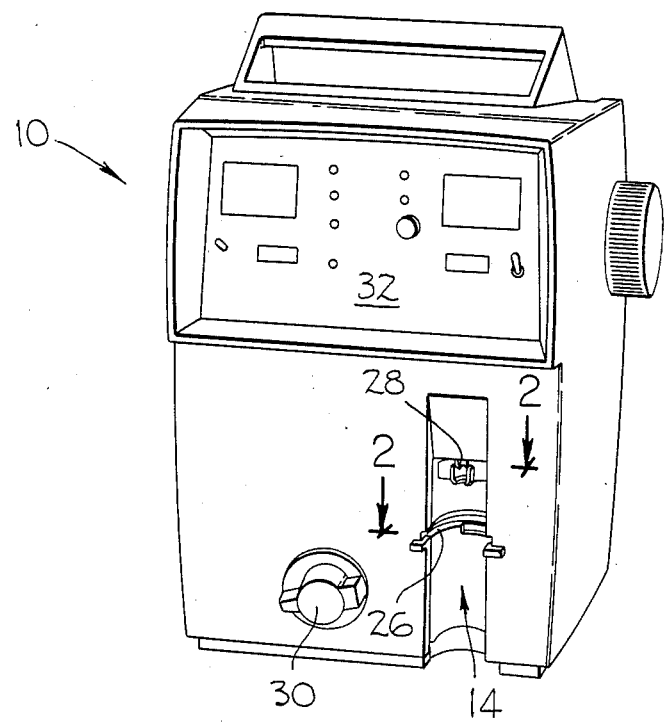
FIG. 1 is an isometric view of a pump driver mechanism of a type adapted to accept the cassette of the present invention.

FIG. 1 shows a generally conventional pump driver mechanism 10 which includes a recessed chamber 14 on the front face thereof for receiving a disposable cassette 12 (shown in detail in FIG. 4).

In practice, a cassette 12 will be charged with I.V. fluid and then placed within the chamber 14 for use with a single patient whereby it will be disposed of after such use and replaced with another cassette.

As can be seen from FIG. 4, the I.V. pump cassette of the present invention generally comprises a rigid plastic body including an enclosed pumping chamber 16 with the body being provided with a generally horizontally extending support portion 18 which extends laterally from the mid-portion of the cassette in order to support the cassette in an upright position in the pump driver mechanism 10. Reciprocably mounted in the pumping chamber 16 at the upper end of the cassette is a plunger 20 which includes at its uppermost end a rounded protuberance 21. Extending upwardly from the support portion 18 of the body is a cylindrical inlet sleeve 23 and extending downwardly at the lower end thereof is a cylindrical outlet sleeve 24, both of said inlet and outlet sleeves being adapted to be connected to tubing T as shown. As explained previously, the cassette inlet is adapted to be connected to a source of I.V. fluid and the cassette outlet is adapted to be connected to the patient by means of a conventional I.V. administration set including the appropriate tubing, drip chamber, clamp, injection sites and needle adapter. For further details of the construction, and particularly, the interior details of the cassette 12, reference may be had to the aforementioned prior U.S. Pat. No. 4,336,800 to Pastrone.

Referring again to FIG. 1, it will be appreciated that the cassette 12 is adapted to be inserted into the driver 10 so that the support portion 18 will be received in a generally horizontally extending recess 26 in the chamber 14. The protuberance 21 at the upper end of the plunger 20 of the cassette is adapted to slide in and be gripped by a receiver 28 which is mounted to the lowermost end of a reciprocating piston driven by a stepper motor and controlled through conventional circuitry located in the pump driver. When the cassette is inserted into the pump driver mechanism, the knob 30 on the front panel thereof can be turned to lock the cassette therein (by means to be explained in greater detail hereinafter) and the cassette will then be ready to function in its operative mode. The controls for determining the rate at which fluid is pumped from the cassette and the maximum dosage to be delivered therefrom are set in the control panel 32 of the pump driver mechanism as shown.

It will be seen from FIGS. 3 and 4 that the supporting portion 18 of the cassette includes a generally flat undersurface which is adapted to rest upon a generally flat supporting surface 38 of the recess 26 (FIG. 3). The outer circumference of the support portion 18 will be seen to be formed by a raised wall 40 which is provided on opposite sides of the cassette with a pair of opposed indentations 43 and which is further provided with an opposed pair of upwardly facing recesses 42 (one only being shown in FIG. 4). When the cassette is fully inserted into the driving mechanism in its operative position, latching members (not shown) are provided to pop into the recesses 43 while overhead clamping members 46 (shown in FIG. 3) are adapted to be moved downwardly upon rotation of the knob 30 in order to clamp the cassette firmly in such operable position within the chamber 14 of the pump driving mechanism.

It will be noted (FIG. 4) that the trailing end 48 of the support portion 18 of the cassette is enlarged so that it might be gripped by the fingers to enable the cassette to be readily inserted within the recess 26 of the pump driver. When the cassette is fully inserted, only the trailing portion 48 of the cassette will be exposed at the exterior portion of chamber 14 with the generally semicircular forward portion of the cassette being received well within the recess 26 at the innermost end of chamber 14.

Referring now to FIG. 3, it will be noted that the semicylindrical inner wall 50 of the recess 14 is provided with a recessed portion 52 at the inner end thereof which terminates in a lower horizontally extending wall 53. As can be seen, when the cassette is inserted, the body of the cassette (shown in phantom lines in FIG. 3) is adapted to be received beneath the wall 53 when it is pushed all of the way into the recess 14. In this operative position of the cassette, the protuberance 21 will be grippingly received by the receiver 28, and the clamping members 46 may be lowered into the associated recesses 42 at the sides of the cassette.

In accordance with the present invention, a switch activator 60 is provided at the forward edge of the support portion 18 of the cassette, as is shown in FIG. 4. This activator is in the form of a semicircular upstanding fence which is provided with a plurality of enlarged portions or ribs 61 about the periphery thereof so as to provide it with good rigidifying support. The fence is formed of a hard polycarbonate plastic material which is ultrasonically welded to the upper flat face of the support portion 18. As seen in FIG. 3, the fence does not extend upwardly so far that it cannot be received under the lower wall 53 of the inner recess 52. However, in those pump driver mechanisms where it is not desired that the cassette be received, the wall 53 will extend lower so as to interfere with the activator 60 on both sides thereof as the cassette is inserted toward its operative position. Due to the deflection resisting shape of the activator, complete insertion of such cassette will be prevented. Thus, the particular cassette 12, which in the current embodiment of the invention is to be used only for low volume applications, will be capable of use only in pump driver mechanisms 10 specially designed for such applications.

Figure 2:
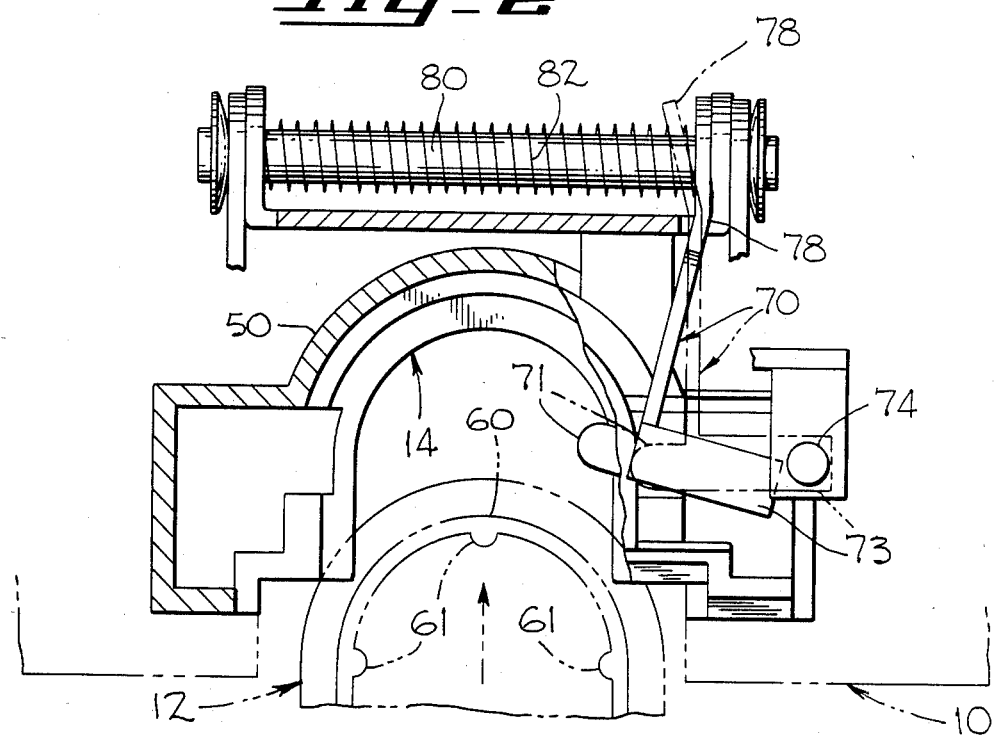
FIG. 2 is an enlarged section through the cassette receiving chamber taken generally along the line 2—2 of FIG. 1 and showing in phantom lines the forward portion of a cassette during insertion and the deflected position of the switch arm.

In accordance with the present invention the switch activator or fence 60 performs a second function when it is inserted into a proper pump driver mechanism 10, i.e., one which is particularly adapted for low flow operation. In this case, as illustrated in the pump driver 10 disclosed herein, the fence 60 will activate a switch mechanism that functions to signal the pump driver controls that the proper cassette has been received therein thereby enabling the driver mechanism for operation. Thus, a laterally pivotable switch arm 70 is provided at one side of the recess 14 (FIG. 2) which arm includes a lowermost projecting finger 71. As shown in the full line position of FIG. 2, this lower finger will be in the path of the arcuately curved face of switch activator 60 as the cassette is inserted. As the cassette moves past the finger 71, it will be pushed outwardly to the phantom line position of FIG. 2. As seen in FIGS. 2 and 4, the uppermost end of switch arm 70 includes an outwardly extending finger 73 which, when the switch arm is moved to its deflected position, will be received between an LED light source 74 and a photodetector 75 so as to break the light beam therebetween. When this beam is broken, conventional detection circuitry can be used to provide an enabling signal to the control circuitry in the pump driver 10 so as to permit the pump cassette to thereafter function in its normal fashion in pumping I.V. liquid.

As shown in FIG. 4, the LED 74 and photodetector 75 are mounted on a U-shaped bracket which can be attached in a suitable fashion to the frame structure of the pump driver mechanism. The switch arm 70 further includes an integral rearward extension 78 which is provided with an aperture 79 adapted to be received about a shaft 80 mounted in the pump driver. A spring 82 is provided about the shaft in engagement with the inner face of the extension 78 so as to normally bias the finger 71 inwardly, as seen in FIG. 2. When the cassette is inserted the extension 78 will compress the spring 82 along shaft 80 as will be obvious, and, when the cassette is removed from the pump driver, the spring 82 will cause the switch arm to pivot so as to return the finger 71 to its inwardly projecting position.

It will be seen that the present invention permits a conventional cassette to be uniquely usable with one class of pump driver mechanisms and uniquely non-usable with a second class of pump driver mechanisms while retaining its same basic operative components. The switch activator or fence 60 provides a dual function of both serving as a blocking member and as a switch activator in a relatively simple and yet highly effective manner.

Although the best mode contemplated for carrying out the present invention has been herein shown and described, it will be apparent that modification and variation may be made without departing from what is regarded to be the subject matter of the invention.

What is claimed is:

1. A cassette for pumping liquids to be fed intravenously to a patient comprising a rigid body enclosing a pumping chamber, said chamber including an inlet adapted to be connected to tubing leading to a source of I.V. liquid and an outlet adapted to be connected to tubing leading to the patient, said body including a mounting portion extending laterally from the body in a generally horizontal plane and serving to support the body on opposite sides thereof in a pump driver mechanism with said inlet being located at the upper end of the body and said outlet being located at the lower end of the body, a pumping member reciprocably mounted in and extending upwardly from the upper surface of the body for periodically reducing the volume of the pumping chamber and thereby pumping liquid therefrom, said pumping member having a protuberance at the upper end thereof for reception by a reciprocable member of the pump driver mechanism, said mounting portion having recesses on the opposed lateral sides thereof adapted to be received by clamping members of said pump driver mechanism to maintain the cassette in locked engagement with said pump driver mechanism, said mounting portion including a rearward extension for adapting the cassette to be gripped for sliding it into an operable position in a pump driver mechanism by placing said lateral sides thereof in supported engagement with the pump driver mechanism and said recesses in position to be received by said clamping members, and an upstanding switch activator fixedly mounted to the forward end of said mounting portion, said activator extending in a semicircular path adjacent to the leading edge of the mounting portion and extending upwardly from the plane of the mounting portion so as to provide a smoothly curved wall that can activate a laterally movable switch arm in said pump driver mechanism as the cassette is moved to its operable position and that provides a rigid structure which will resist inward deflection to prevent the cassette from being inserted into an operable position in the wrong pump driver mechanism.

2. A cassette according to claim 1 wherein said switch activator includes a plurality of upwardly extending enlarged rib portions for reinforcing said activator to resist said inward deflection.

3. A cassette according to claim 1 wherein said switch activator is comprised of a rigid plastic material.

4. A cassette according to claim 1 wherein said activator extends upwardly from said mounting portion to an elevation above that of the pumping chamber.

5. For use with a pump driving mechanism for pumping liquids to be fed intravenously to a patient, said mechanism including a reciprocable member, a motor for driving said reciprocable member, a pair of vertically movable clamping members for receiving a pump chamber cassette, and a pivotable switch arm positioned adjacent to said clamping members; a cassette comprising a rigid body enclosing a pumping chamber, said chamber including an inlet adapted to be connected to tubing leading to a source of I.V. liquid and an outlet adapted to be connected to tubing leading to the patient, said body including a mounting portion extending laterally from the body in a generally horizontal plane and serving to support the body on opposite sides thereof in the pump driver mechanism with said inlet being located at the upper end of the body and said outlet being located at the lower end of the body, a pumping member reciprocably mounted in and extending upwardly from the upper surface of the body for periodically reducing the volume of the pumping chamber and thereby pumping liquid therefrom, said pumping member having a protuberance at the upper end thereof for reception by said reciprocable member of the pump drive mechanism, said mounting portion having recesses on the opposed lateral sides thereof adapted to be received by said clamping members to maintain the cassette in locked engagement with said pump driver mechanism, said mounting portion including a rearward extension for adapting the cassette to be gripped for sliding it into an operable position in a pump driver mechanism by placing said lateral sides thereof in supported engagement with the pump driver mechanism and said recesses in position to be received by said clamping members, and an upstanding switch activator fixedly mounted to the forward end of said mounting portion, said activator extending in a semicircular path adjacent to the leading edge of the mounting portion and extending upwardly from the plane of the mounting portion so as to provide a smoothly curved wall that is adapted to engage said switch arm and cause it to pivot laterally to activate the pump driver mechanism as the cassette is moved to its operable position.

6. In a cassette for pumping liquids to be fed intravenously to a patient comprising a rigid body enclosing a pumping chamber, said chamber including an inlet adapted to be connected to tubing leading to a source of I.V. liquid and an outlet adapted to be connected to tubing leading to the patient, said body including a mounting portion extending laterally from the body in a generally horizontal plane and serving to support the body on opposite sides thereof in a pump driver mechanism with said inlet being located at the upper end of the body and said outlet being located at the lower end of the body, a pumping member reciprocably mounted in and extending upwardly from the upper surface of the body for periodically reducing the volume of the pumping chamber and thereby pumping liquid therefrom, said pumping member having a protuberance at the upper end thereof for reception by a reciprocable member of the pump driver mechanism, said mounting portion having recesses on the opposed lateral sides thereof adapted to be received by clamping members of said pump driver mechanism to maintain the cassette in locked engagement with said pump driver mechanism, said mounting portion including a rearward extension for adapting the cassette to be gripped for sliding it into an operable position in a pump driver mechanism by placing said lateral sides thereof in supported engagement with the pump driver mechanism and said recesses in position to be received by said clamping members, the improvement comprising an upstanding switch activator fixedly mounted to the forward end of said mounting portion, said activator extending in a semicircular path adjacent to the leading edge of the mounting portion and extending upwardly from the plane of the mounting poriton so as to provide a smoothly curved wall that can activate a laterally movable switch arm in said pump driver mechanism as the cassette is moved to its operable position and that provides a rigid structure which will resist inward deflection to prevent the cassette from being inserted into an operable position in the wrong pump driver mechanism.

7. In a cassette according to claim 6 wherein said switch activator includes a plurality of upwardly extending enlarged rib portions for reinforcing said activator.

8. In a cassette according to claim 6 wherein said switch activator is comprised of a rigid plastic material.

9. I.V. pumping apparatus for pumping liquids to be fed intravenously to a patient comprising a pump driver mechanism including a motor; means for operating and controlling said motor; a reciprocable member operatively connected to said motor and having an enlarged receiver at the lower end thereof, said driver mechanism having a recess on one face thereof into which said receiver extends; clamping members positioned adjacent opposed sides of said recess; a switch arm mounted for lateral movement adjacent one side of said recess; a switch activated by said switch arm to enable said operating and controlling means; and a cassette comprising a rigid body enclosing a pumping chamber, said chamber including an inlet adapted to be connected to tubing leading to a source of I.V. liquid and an outlet adapted to be connected to tubing leading to the patient, said body including a mounting portion extending laterally from the body in a generally horizontal plane and serving to support the body in said driver mechanism recess with said inlet being located at the upper end of the body and said outlet being located at the lower end of the body, a pumping member reciprocably mounted in and extending upwardly from the upper surface of the body for periodically reducing the volume of the pumping chamber and thereby pumping liquid therefrom, said pumping member having a protuberance at the upper end thereof for reception by said reciprocable member of the pump driver mechanism, said mounting portion having recesses on the opposed lateral sides thereof adapted to be received by said clamping members to maintain the cassette in locked engagement, said mounting portion including a rearward extension for adapting the cassette to be gripped for sliding it into an operable position in said recess by placing said lateral sides thereof in supported engagement within said recess in position to be received by said clamping members, and an upstanding switch activator fixedly mounted to the forward end of said mounting portion, said activator extending in a semicircular path adjacent to the leading edge of the mounting portion and extending upwardly from the plane of the mounting portion so as to provide a smoothly curved wall that is arranged to engage said switch arm as the cassette is moved to its operable position.

10. I.V. pumping apparatus according to claim 9 wherein said switch arm comprises a vertically extending member having a horizontally projecting extension at its lower end adapted to be engaged by said switch activator and a horizontally projecting extension at its upper end adapted to activate said switch.

11. I.V. pumping apparatus according to claim 10 wherein said switch comprises a light activated photodetector with said switch arm being moved in a path into and out of light blocking registration with the photodetector.

12. I.V. pumping apparatus according to claim 10 including a spring for normally biasing said switch arm into a position wherein said lower horizontal extension thereof extends into the path of the cassette switch activator.

* * * * *